(12) United States Patent
Qian et al.

(10) Patent No.: US 11,969,705 B2
(45) Date of Patent: Apr. 30, 2024

(54) IRREVERSIBLE COVALENT ORGANIC FRAMEWORK FOR EFFICIENT AND SELECTIVE GOLD RECOVERY AND PREPARATION METHOD THEREOF

(71) Applicant: Jiangnan University, Wuxi (CN)

(72) Inventors: Hailong Qian, Wuxi (CN); Fanlin Meng, Wuxi (CN); Xiuping Yan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 741 days.

(21) Appl. No.: 17/113,525

(22) Filed: Dec. 7, 2020

(65) Prior Publication Data

US 2021/0086164 A1 Mar. 25, 2021

Related U.S. Application Data

(63) Continuation of application No. PCT/CN2019/113170, filed on Oct. 25, 2019.

(30) Foreign Application Priority Data

Sep. 30, 2019 (CN) .......................... 2019109437863

(51) Int. Cl.
*B01J 20/22* (2006.01)
*B01J 20/30* (2006.01)
(Continued)

(52) U.S. Cl.
CPC ......... *B01J 20/226* (2013.01); *B01J 20/3085* (2013.01); *C07D 403/14* (2013.01); *C22B 7/006* (2013.01); *C22B 11/046* (2013.01)

(58) Field of Classification Search
None
See application file for complete search history.

(56) References Cited

U.S. PATENT DOCUMENTS

2020/0360892 A1\* 11/2020 Ma ...................... B01J 20/3212
2021/0002426 A1\* 1/2021 Strano .................... C08G 69/32

FOREIGN PATENT DOCUMENTS

CN 108822301 A 11/2018

OTHER PUBLICATIONS

Rowan, S.J., Cantrill, S.J., Cousins, G.R.L., Sanders, J.K.M. and Stoddart, J.F. (2002), Dynamic Covalent Chemistry. Angew. Chem. Int. Ed., 41: 898-952. https://doi.org/10.1002/1521-3773(20020315)41:6<898::AID-ANIE898>3.0.CO;2-E (Year: 2002).\*

\* cited by examiner

*Primary Examiner* — Chester T Barry
(74) *Attorney, Agent, or Firm* — IPRO, PLLC (57) ABSTRACT

The disclosure discloses an irreversible covalent organic framework for efficient and selective gold recovery and a preparation method thereof, and belongs to the technical field of precious metal recovery from an aqueous solution. In the disclosure, metal trifluoromethanesulfonate is used as a catalyst, and a solvothermal method is used to prepare a mother covalent organic framework, and then the corresponding structural unit is used to perform an exchange reaction to prepare an irreversible amide-linked covalent organic framework material. The disclosure solves the problem of preparation of high-stability irreversible covalent organic framework, the introduced amide bond gives the covalent organic framework the ability to quickly and selectively recover precious metal gold from an aqueous solution, and the covalent organic framework can be used repeatedly. The application of the covalent organic framework as an efficient adsorbent in the field of adsorption and separation is expanded, and a new material is provided for efficient recovery or removal of metal salts.

7 Claims, 7 Drawing Sheets

(51) Int. Cl.
*C07D 403/14* (2006.01)
*C22B 7/00* (2006.01)
*C22B 11/00* (2006.01)

IRREVERSIBLE COVALENT ORGANIC FRAMEWORK FOR EFFICIENT AND SELECTIVE GOLD RECOVERY AND PREPARATION METHOD THEREOF

TECHNICAL FIELD

The disclosure specifically relates to an irreversible covalent organic framework for efficient and selective gold recovery and a preparation method thereof, and belongs to the technical field of precious metal recovery from an aqueous solution.

BACKGROUND

Though best-known as jewelry, gold actually possesses wide application in our daily life in the fields of electronics, medicine, and catalysis. The huge consumption of gold leads to low abundance of the precious metal recourse and massive risk to ecology. Hence, the recovery of gold from secondary resources such as the waste of electronic equipment demonstrates extreme importance in view of the economy and environment. Currently, plenty of technologies involving adsorption, precipitation, solvent extraction and ion exchange have been developed to recover gold from an aqueous solution. The adsorption approach with porous materials as adsorbents attracts wide attention on account of its eco-friendliness, low cost, and easy operation. Adsorbents, as the core of adsorption, have direct effect on adsorption performance. At present, various materials have been used for gold recovery, such as metal organic frameworks (MOFs), organic polymers, nano-particles and biomass materials. However, a majority of these adsorbents suffer from terrible kinetics with several hours or even days to reach adsorption equilibrium. Additionally, the poor selectivity, low loading capacity and lacking stability also go against the efficient recovery of gold. Consequently, it is essential to design adsorbents with rapid kinetics, large capacity and high stability for selective gold recovery.

Covalent organic frameworks (COFs) are known as a kind of crystalline porous materials linked with reversible covalent bonds, showing wide potential in the fields of gas storage, catalysis, sensing and separation. The stability of COFs plays a pushing role in the application of COFs. However, typical COFs are formed on the basis of dynamic covalent chemistry. The reversible covalent linkage is the nub of the formation of crystallinity as well as an important factor affecting the stability of COFs. Hence, construction of COFs with irreversible bonds is crucial in developing highly stable materials. But the typical preparation method cannot prepare irreversible covalent bonds. Therefore, it is necessary to develop an effective method to prepare irreversible and highly stable covalent organic framework materials.

SUMMARY

The disclosure discloses a preparation method of an irreversible covalent organic framework material, and the method includes the following steps:

(1) under the action of a catalyst, first performing a condensation reaction on a triamino compound represented by formula I-1 and a p-dicarboxaldehyde compound represented by formula II-1; and (2) then adding and mixing a p-diformyl chloride compound represented by formula III-1 for performing an exchange reaction;

or,

(1) under the action of a catalyst, first performing a condensation reaction on a p-diamino compound represented by formula I-2 and a tricarboxaldehyde compound represented by formula II-2; and

(2) then adding and mixing a triformyl chloride compound represented by formula III-2 for performing an exchange reaction;

wherein, A is selected from nitrogen, benzene ring and s-triazine ring; and B is selected from phenyl, biphenyl and triphenyl.

In an embodiment of the disclosure, the design route for synthesizing the framework material in the method is as follows:

-continued

Amide-linked COF
JNU-1

The disclosure also discloses an irreversible covalent organic framework material for highly selective gold recovery: A triamino compound represented by formula I-1 and a p-dicarboxaldehyde compound represented by formula II-1 are used as structural units to form a covalent organic framework material, and then a p-diformyl chloride compound represented by formula III-1 is used for exchange to obtain a COFs covalent organic framework material with an amide structure; or, a p-diamino compound represented by formula I-2 and a tricarboxaldehyde compound represented by formula II-2 are used as structural units to form a covalent organic framework material, and then a triformyl chloride compound represented by formula III-2 is used for exchange to obtain a covalent organic framework material with an amide structure;

formula II-2 formula III-2

ClOC—B—COCl formula III-1 wherein, A is selected from nitrogen, benzene ring and s-triazine ring; and B is selected from phenyl, biphenyl and triphenyl.

In an embodiment of the disclosure, the catalyst in step (1) is a metal trifluoromethanesulfonate, specifically examples including scandium trifluoromethanesulfonate and/or ytterbium trifluoromethanesulfonate.

In an embodiment of the disclosure, the unit structure of the irreversible covalent organic framework material is as follows:

Amide-linked COF
JNU-1

In an embodiment of the disclosure, the condensation reaction in step (1) is carried out in an organic solvent, and the organic solvent includes one or a mixture of more of dioxane, mesitylene, tetrahydrofuran and N,N-dimethylacetamide.

In an embodiment of the disclosure, the condensation reaction in step (1) forms an imine-linked covalent organic framework material (TzBA).

In an embodiment of the disclosure, the exchange reaction in step (2) obtains a covalent organic framework material (JNU-1) having an amide structure.

In an embodiment, the molar ratio of the triamino compound to the p-dicarboxaldehyde compound is 2:3. The molar ratio of the tricarboxaldehyde compound to the p-diamino compound is 2:3.

In an embodiment, the amount of the catalyst used is 5-10% of the total mass of two reactants as structural units.

In an embodiment, the solvent used to prepare the covalent organic framework is a mixed solvent of dioxane and mesitylene, and the amount-to-volume ratio is 2:1.

In an embodiment, the p-diformyl chloride compound equivalent to the p-dicarboxaldehyde compound or the triformyl chloride compound equivalent to the tricarboxaldehyde compound is added for the exchange reaction.

In an embodiment, the temperature of the exchange reaction is 4-25° C.

In an embodiment of the disclosure, the preparation method adopts a monomer exchange method to prepare an amide-linked covalent organic framework with high stability and crystallinity, and realizes efficient and selective gold recovery from an aqueous solution. The preparation method specifically includes the following steps: dissolving 4,4',4"-(1,3,5-triazine-2,4,6-triyl)trianiline, 4,4'-biphenyldicarboxaldehyde, and scandium trifluoromethanesulfonate respectively in dioxane and mesitylene, performing ultrasonic treatment to obtain a uniformly mixed solution, and reacting the above reaction solution at 60° C. for 1 day; after a reaction tube cools to room temperature, adding terephthaloyl chloride, performing ultrasonic treatment for 10 minutes and reaction at 4° C. for 2 days; centrifuging and cleaning the obtained red solid with tetrahydrofuran; performing Soxhlet extraction and cleaning with acetone; and finally performing vacuum drying to obtain the amide-linked covalent organic framework JNU-1 with a yield of 82.6%.

The disclosure also discloses a method for selectively adsorbing gold ions, and the method uses the above covalent organic framework as an adsorbent.

In an embodiment of the disclosure, the method for adsorbing gold ions includes the following steps:

placing the adsorbent in an aqueous solution of gold, adding acid, uniformly mixing and centrifuging the mixed solution, and recovering and eluting solid powder to obtain the gold adsorbed on the covalent organic framework.

In an embodiment of the disclosure, the acid concentration in the solution after adding acid is 1-2 mol/L.

In an embodiment of the disclosure, the acid includes hydrochloric acid, sulfuric acid, and nitric acid.

In an embodiment of the disclosure, the eluent used in elution is a thiourea hydrochloride solution.

In an embodiment of the disclosure, the concentration of the thiourea hydrochloride solution is 1-2 mol/L.

The disclosure also discloses an application of the irreversible covalent organic framework material in the fields of gas storage, catalysis, sensing and separation.

In the disclosure herein, an irreversible amide-linked covalent organic framework with high crystallinity and stability is obtained by replacing an imine bond in the imine-linked covalent organic framework with an amide bond. The introduced amide bond gives the prepared covalent organic framework the ability to quickly and highly selectively adsorb gold from an aqueous solution, and the prepared covalent organic framework can be used to selectively recover precious metal gold from an aqueous solution.

The disclosure solves the problem of preparing an irreversible covalent organic framework material with high stability, and the prepared amide-linked covalent organic framework material has high crystallinity and stability. Protonated amide bonds can form hydrogen bonds with gold ions in the aqueous solution, and the prepared amide-linked covalent organic framework material has the advantages of high binding ability to gold, fast adsorption kinetics, high selectivity, large adsorption capacity and repeatable use of material. The adsorption of gold from an aqueous solution can reach adsorption equilibrium within 10 seconds, and the maximum gold adsorbing capacity can reach 1124 mg $g^{-1}$. When the concentration of interfering ions is the same as that of gold, JNU-1 can still maintain an adsorption efficiency of 80% or above. When the concentration of interfering ions is 10 times that of gold, JNU-1 can still maintain an adsorption efficiency of 70% or above. After four repetitions, it can still maintain an adsorption efficiency of 85% or above.

DETAILED DESCRIPTION

Example 1

Preparation of an amide-linked covalent organic framework for efficient and selective gold recovery: the amide-linked covalent organic framework with high stability and crystallinity is prepared by a monomer exchange method to realize efficient and selective recovery of gold from an aqueous solution, including the following steps:

1) 36.4 mg (0.10 mmol) of 4,4',4"-(1,3,5-triazine-2,4,6-triyl)trianiline (Tz), 34.5 mg (0.164 mmol) of 4,4'-biphenyldicarboxaldehyde (BA), and 3.5 mg of scandium trifluoromethanesulfonate are dissolved in a mixed solvent of dioxane and mesitylene (2:1, 3 mL) respectively, ultrasonic treatment is performed to obtain a uniformly mixed solution, and the reaction solution is reacted at 60° C. for 1 day;

2) after a reaction tube cools to room temperature, 30.5 mg (0.15 mmol) of terephthaloyl chloride is added, ultrasonic treatment is performed for 10 minutes and then reaction is performed at 4° C. for 2 days to obtain red solid; and the obtained red solid is centrifuged and cleaned with 10 mL of tetrahydrofuran thrice, subjected to Soxhlet extraction and cleaning with acetone, and finally vacuum dried to obtain the amide-linked covalent organic framework JNU-1 with a yield of 82.6%.

Figure 1:
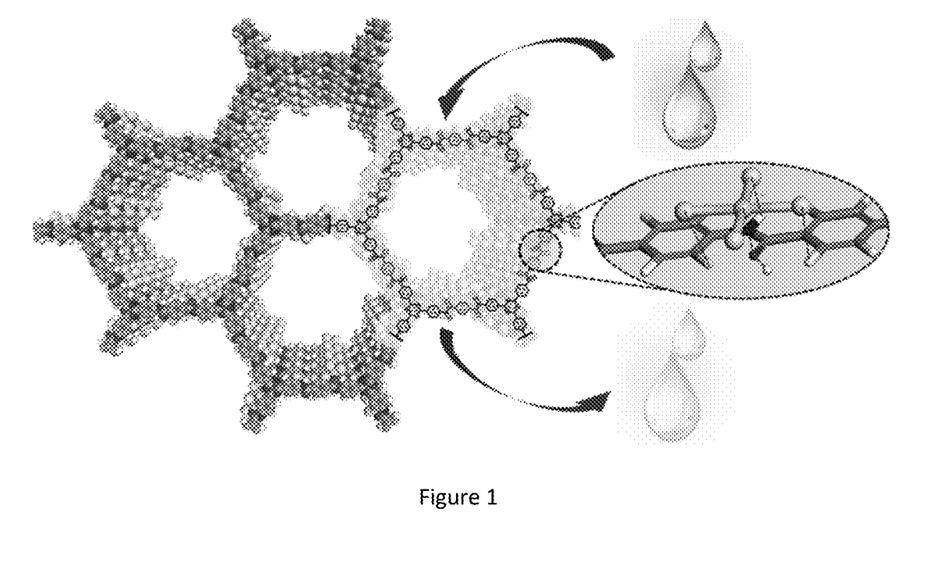
FIG. 1 is a schematic diagram of the structure of an amide-linked covalent organic framework prepared in Example 1.

FIG. 1 is a schematic diagram of an amide-linked covalent organic framework for efficient and selective gold recovery prepared in the present example.

Figure 2A:
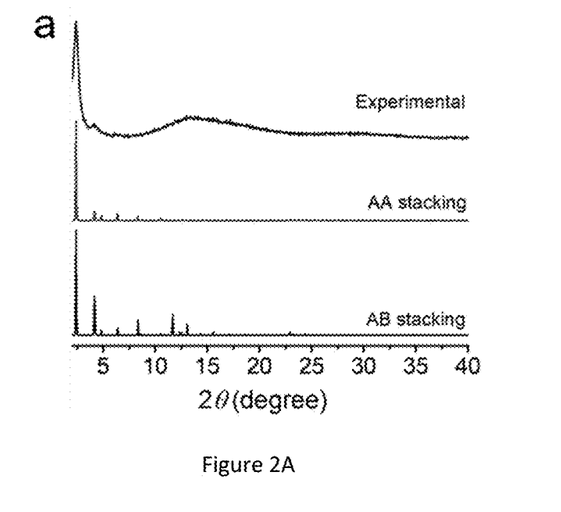
FIG. 2A is an experimental and simulated X-ray powder diffraction pattern of the mother covalent organic framework TzBA prepared in Example 1.
Figure 2B:
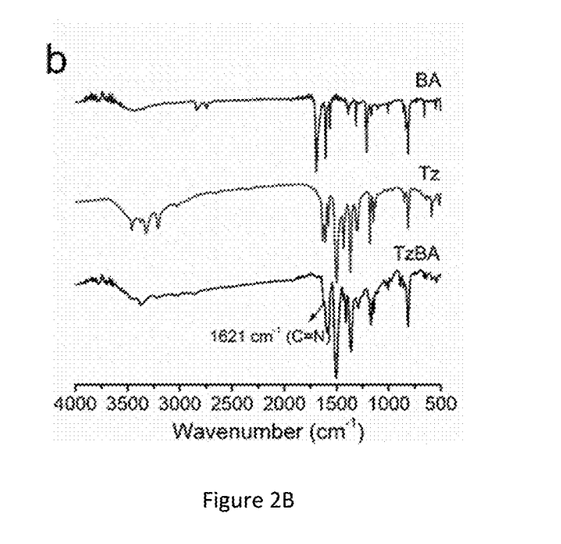
FIG. 2B is an infrared spectrum of the monomers Tz and BA and the prepared TzBA.

FIG. 2A is an experimental and simulated X-ray powder diffraction pattern of the mother covalent organic framework TzBA prepared in the present example, and FIG. 2B is an infrared spectrum of the monomers Tz and BA used in the experiment and the prepared TzBA. It can be seen from FIG. 2A that the diffraction peaks of the prepared TzBA are similar to the simulated diffraction peaks of an AA stacking layer structure, indicating that the prepared TzBA is of an AA stacking layer structure. The appearance of the imine bond vibration peak at 1621 $cm^{-1}$ in FIG. 2B proves that the prepared covalent organic framework is of imine linkage.

Figure 3A:
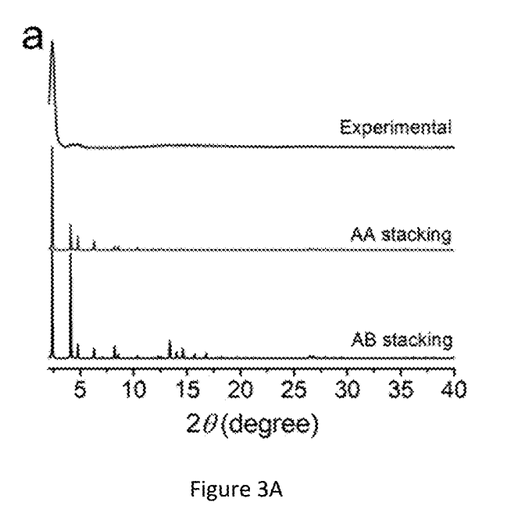
FIG. 3A is an experimental and simulated X-ray powder diffraction pattern of the covalent organic framework JNU-1 prepared in Example 1.
Figure 3B:
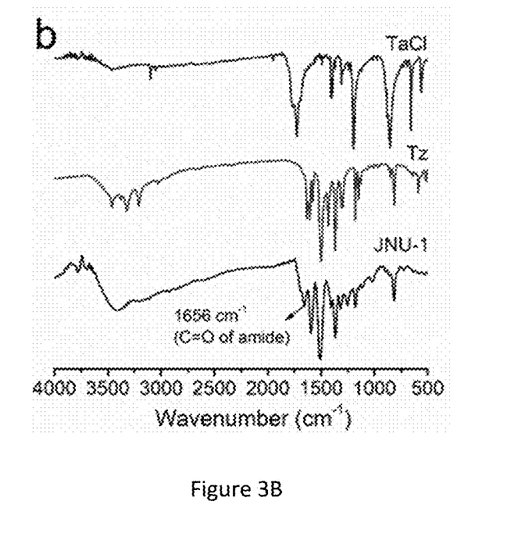
FIG. 3B is an infrared spectrum of the monomers Tz and TaCl and the prepared JNU-1.

FIG. 3A is an experimental and simulated X-ray powder diffraction pattern of the covalent organic framework JNU-1 prepared in the present example, and FIG. 3B is an infrared spectrum of the monomers Tz and TaCl used in the experiment and the prepared JNU-1. It can be seen from FIG. 3A that the diffraction peaks of the prepared JNU-1 are similar to the simulated diffraction peaks of an AA stacking layer structure, indicating that the prepared JNU-1 is of an AA stacking layer structure. The appearance of the amide bond vibration peak at 1656 $cm^{-1}$ in FIG. 3B proves that the prepared covalent organic framework is of amide linkage.

Figure 4A:
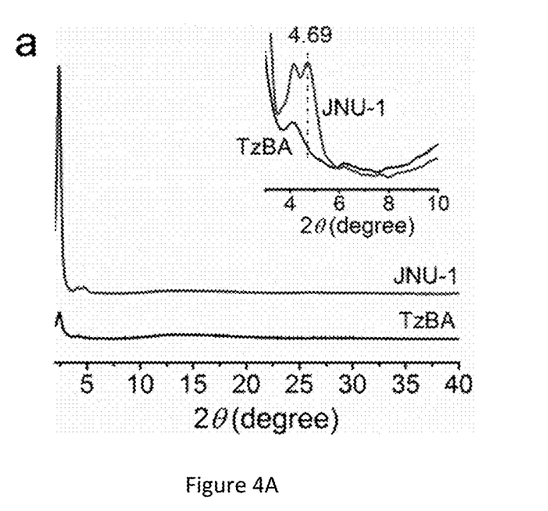
FIG. 4A is a powder X-ray diffraction pattern of the amide-linked covalent organic framework JNU-1 prepared after the exchange of the mother covalent organic framework TzBA prepared in Example 1 with a monomer.
Figure 4B:
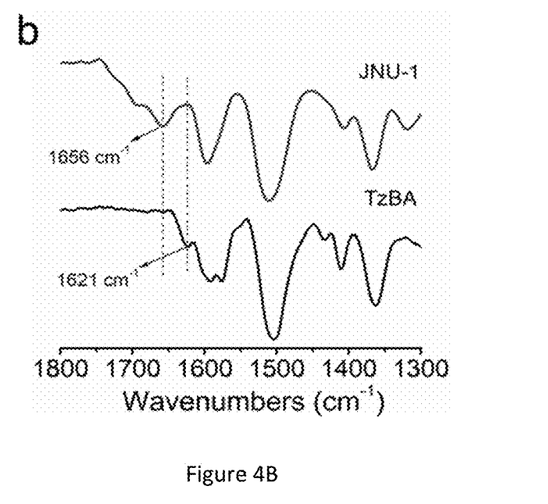
FIG. 4B is an infrared spectrum of the amide-linked covalent organic framework JNU-1 prepared after the exchange of the mother covalent organic framework TzBA prepared in Example 1 with the monomer.

FIG. 4A is a powder X-ray diffraction pattern of the amide-linked covalent organic framework JNU-1 prepared after the exchange of the mother covalent organic framework TzBA prepared in the present example with a monomer, and FIG. 4B is an infrared spectrum of the amide-linked covalent organic framework JNU-1 prepared after the exchange of the mother covalent organic framework TzBA prepared in the present example with the monomer. It can be seen from FIG. 4A that a new diffraction peak appears at 4.69 degrees, indicating the success of the exchange process. The main diffraction peak intensity of the JNU-1 after exchange is much higher than that of the TzBA, indicating that the crystallinity of the material is greatly improved after exchange. Disappearance of the peak of the imine bond and appearance of the peak of the amide bond after the exchange in FIG. 4B indicate the success of the exchange process.

Figure 5:
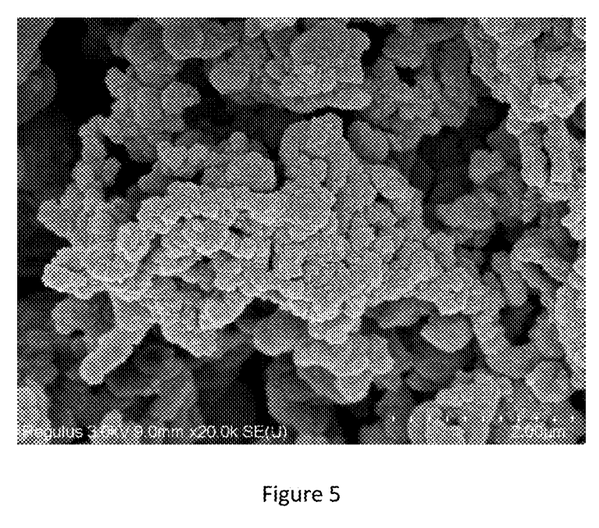
FIG. 5 is a scanning electron micrograph of JNU-1 prepared in Example 1.

FIG. 5 is a scanning electron micrograph of JNU-1 prepared in the present example.

Example 2

Preparation of an amide-linked covalent organic framework for efficient and selective gold recovery: the steps and methods are basically the same as that in Example 1, and the difference is that the 4,4',4"-(1,3,5-triazine-2,4,6-triyl)trianiline and 4,4'-biphenyldicarboxaldehyde in step 1) are replaced with 1,3,5-tris(4-formyl-phenyl)triazine and p-phenylenediamine, and in step 2), the terephthaloyl chloride is replaced with 1,3,5-trimesoyl chloride, and the other conditions remain unchanged:

The characterization results of the prepared covalent organic framework are similar to those of Example 1, and the yield of the obtained amide-linked covalent organic framework is 87.2%.

Example 3: Application in Adsorption and Recovery of Gold Ions

The amide-linked covalent organic framework prepared in Example 1 is used as an adsorption material. 1 mg of JNU-1 is taken and placed in 1 mL of a series of aqueous solutions with known gold ion concentrations (43-1181 mg $L^{-1}$) and containing 2 mol $L^{-1}$ hydrochloric acid and ultrasonic treatment is performed for 1 minute. Solid powder is recovered by centrifugation, and the covalent organic framework is eluted with 2 mL of a 1 mol $L^{-1}$ acidic thiourea hydrochloride solution.

Figure 6A:
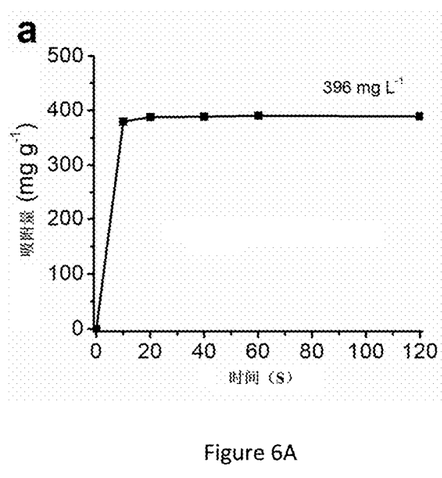
FIG. 6A shows the adsorption kinetic curve of JNU-1 against gold.

FIG. 6A is an adsorption kinetic curve of JNU-1 against gold ions. It can be seen from the curve that the prepared amide-linked covalent organic framework can achieve adsorption equilibrium within 10 seconds for the adsorption of gold ions, indicating that the material has an ultra-high adsorption rate.

Figure 6B:
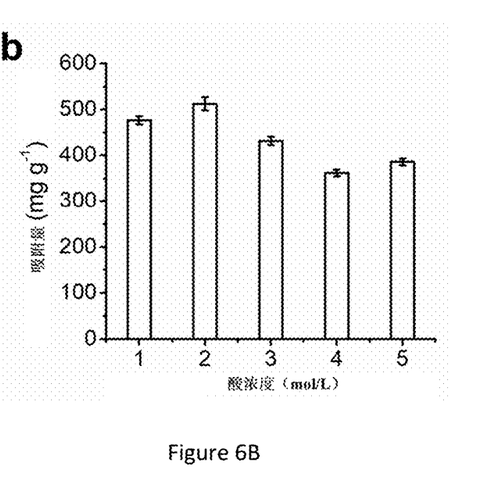
FIG. 6B shows the effect of hydrochloric acid concentration on gold recovery.

FIG. 6B shows the effect of acid concentration in an aqueous solution on the adsorption of gold ions: gold in the aqueous solution is adsorbed under different acidity conditions, and the results show that when the acid concentration is 2 mol $L^{-1}$, the material has the largest adsorption capacity for gold ions.

Figure 6C:
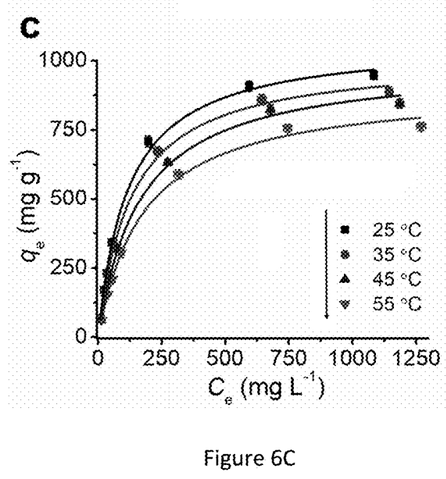
FIG. 6C shows the adsorption isotherm of JNU-1 against gold at 25° C.-55° C.

FIG. 6C shows the adsorption isotherms of JNU-1 for gold after solutions with different gold ion concentrations are adsorbed for 10 min at different temperatures ranging from 25° C. to 55° C. It can be seen from the adsorption isotherms at different temperatures that the increase in temperature is not conducive to the adsorption of gold. The adsorption curve of the prepared JNU-1 for gold satisfies the Langmuir adsorption model, and the maximum adsorption capacity of the JNU-1 for gold calculated by the model is 1124 mg $g^{-1}$.

Figure 6D:
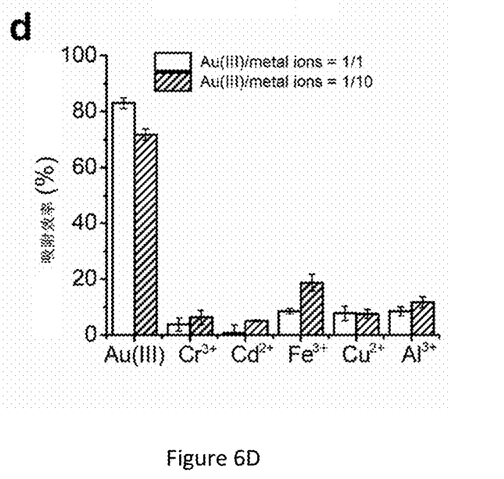
FIG. 6D shows the effect of the concentration of interfering ions on the selective gold recovery rate of JNU-1.

FIG. 6D shows the effect of the concentration of interfering ions on the selective gold recovery rate of JNU-1: ions of different concentrations are adsorbed simultaneously with gold ions, and the results show that when the concentration of interfering ions is the same as that of gold ions, JNU-1 can still maintain an adsorption efficiency of 80% or above. When the concentration of interfering ions is 10 times that of gold ions, JNU-1 can still maintain an adsorption efficiency of 70% or above, indicating that JNU-1 has high selectivity.

Example 4: Repeatability Test

Figure 7:
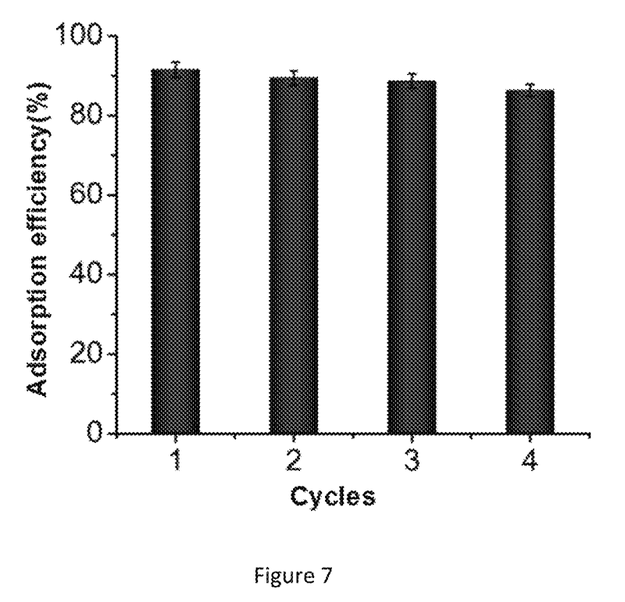
FIG. 7 shows repetitive gold recovery of JNU-1 prepared in Example 1.

After vacuum drying the eluted JNU-1 in Example 3, the JNU-1 is continuously used for the next step of gold adsorption. The results show that the prepared JNU-1 can still maintain an adsorption efficiency of 85% or above after four repetitions, indicating that the prepared material has a high reusable effect (as shown in FIG. 7).

Comparative Example 1

Referring to Example 3, the adsorption material is replaced with a mother imine-linked covalent organic framework TzBA, and other conditions are unchanged to perform adsorption.

1 mg of TzBA is taken and placed in 1 mL of aqueous solution, and the solution is stirred and ultrasonic treated for 1 min; then solid powder is recovered by centrifugation, and the covalent organic framework is eluted with 2 mL of a 1 mol $L^{-1}$ acidic thiourea solution. The maximum adsorption capacity calculated by the Langmuir model is 415 mg $g^{-1}$. It can be seen that the adsorption of gold ions by the exchanged amide-linked covalent organic framework is significantly improved.

What is claimed is:

1. A method for preparing an irreversible covalent organic framework material, comprising the following steps:
   (1) under action of a catalyst, first performing a condensation reaction on a triamino compound represented by formula I-1 and a p-dicarboxaldehyde compound represented by formula II-1; and
   (2) then adding and mixing a p-diformyl chloride compound represented by formula III-1 for performing an exchange reaction;
   or,
   (1) under action of the catalyst, first performing a condensation reaction on a p-diamino compound represented by formula I-2 and a tricarboxaldehyde compound represented by formula II-2; and
   (2) then adding and mixing a triformyl chloride compound represented by formula III-2 for performing an exchange reaction;

formula I-1

$H_2N-B-NH_2$    formula I-2

$OHC-B-CHO$    formula II-1 formula II-2

$ClOC-B-COCl$    formula III-1 formula III-2 wherein A is selected from nitrogen, benzene ring and s-triazine ring; and B is selected from phenyl, biphenyl and triphenyl.

2. The method of claim 1, wherein the catalyst in step (1) is a metal trifluoromethanesulfonate.

3. The method of claim 1, wherein the condensation reaction in step (1) is carried out in an organic solvent, and the organic solvent comprises one or more of dioxane, mesitylene, tetrahydrofuran and N,N-dimethylacetamide.

4. The method of claim 1, wherein the amount of the catalyst used is 5-10% of a total mass of the two reactants as structural units.

5. The method of claim 1, wherein the p-diformyl chloride compound equivalent of the p-dicarboxaldehyde compound, or the triformyl chloride compound equivalent of the tricarboxaldehyde compound is added for the exchange reaction.

6. The method of claim 1, wherein a temperature of the exchange reaction is 4-25° C.

7. An irreversible covalent organic framework material prepared by the method of claim 1.

\* \* \* \* \*